(12) United States Patent  
Waterman (10) Patent No.: US 7,836,890 B2  
(45) Date of Patent: Nov. 23, 2010

(54) SYSTEMS FOR IMMOBILIZATION OF A PATIENT FOR DIAGNOSIS AND TREATMENT OF BREAST TISSUE

(75) Inventor: Glenn N. Waterman, Salt Lake City, UT (US)

(73) Assignee: Diacor, Inc., Salt Lake City, UT (US)

(*) Notice: Subject to any disclaimer, the term of this patent is extended or adjusted under 35 U.S.C. 154(b) by 1023 days.

(21) Appl. No.: 10/968,368

(22) Filed: Oct. 18, 2004

(65) Prior Publication Data

US 2005/0085722 A1     Apr. 21, 2005

Related U.S. Application Data

(60) Provisional application No. 60/512,551, filed on Oct. 17, 2003.

(51) Int. Cl.
| | |
|---|---|
| A61G 15/00 | (2006.01) |
| A61F 5/37 | (2006.01) |
| A61F 13/00 | (2006.01) |
| A47B 71/00 | (2006.01) |
| A47B 13/00 | (2006.01) |
| A47B 7/00 | (2006.01) |
| A47C 20/00 | (2006.01) |
| A47F 5/12 | (2006.01) |
| A47B 3/00 | (2006.01) |
| A61B 6/04 | (2006.01) |
| A61B 5/05 | (2006.01) |

(52) U.S. Cl. ................. 128/878; 128/845; 128/846; 128/870; 5/600; 5/601; 5/612; 5/613; 5/633; 108/1; 108/6; 108/7; 108/33; 378/37; 600/415

(58) Field of Classification Search ......... 128/845–846, 128/97.1, 99.1, 870; 5/735, 600, 612, 613, 5/633, 601; 378/37; 37/64–65, 147, 84, 37/174, 145, 85, 62, 57; 600/407, 415; 70/78, 70/91; 108/1, 6, 7, 33  
See application file for complete search history.

(56) References Cited

U.S. PATENT DOCUMENTS

| | | | |
|---|---|---|---|
| 3,466,439 A | | 9/1969 | Setala |
| 3,751,028 A | | 8/1973 | Scheininger et al. |
| 4,991,243 A | | 2/1991 | Rottermann |
| 5,484,393 A | * | 1/1996 | McCoy .................... 602/6 |
| 5,537,454 A | | 7/1996 | Korver, II |
| D375,163 S | * | 10/1996 | Lipson et al. ........... D24/183 |

(Continued)

*Primary Examiner*—Michael A. Brown  
*Assistant Examiner*—Brandon Jackson  
(74) *Attorney, Agent, or Firm*—TraskBritt (57) ABSTRACT

A breast-board system, components and methods of use therefore. A generally U-shaped wrist support with a flattened bottom and rounded post like tops that may be used as either a cupping-support or as a grasping-post is mounted on a post atop a tiltable breast-board. A second support having a generally U-shaped cross section mounted on a supporting framework extends from a base, which is rotatably mounted to the tiltable breast-board near the edge thereof. The base includes a portion extending over the edge of the breast-board, and, a slidable locking mechanism on the bottom surface, which may be retracted to slide the mechanism out of a recess located on the breast-board. The support may then be rotated to a desired position and the slidable locking mechanism actuated to engage with a desired recess on the breast-board.

15 Claims, 5 Drawing Sheets

U.S. PATENT DOCUMENTS

| | | | | |
|---|---|---|---|---|
| 5,640,958 | A * | 6/1997 | Bonutti | 600/415 |
| 5,778,047 | A | 7/1998 | Mansfield et al. | |
| 5,806,116 | A | 9/1998 | Oliver et al. | |
| 5,808,468 | A * | 9/1998 | Bis et al. | 324/318 |
| 6,026,812 | A * | 2/2000 | Lipson et al. | 128/882 |
| 6,161,237 | A | 12/2000 | Tang et al. | |
| 6,493,417 | B1 | 12/2002 | Baer et al. | |
| 6,508,181 | B1 | 1/2003 | Odell | |
| 6,615,428 | B1 * | 9/2003 | Pattee | 5/601 |
| 6,671,537 | B1 * | 12/2003 | Bonutti | 600/415 |
| 6,865,411 | B2 * | 3/2005 | Erbel et al. | 600/407 |
| 7,131,769 | B2 * | 11/2006 | Vezina | 378/209 |
| 7,216,383 | B2 * | 5/2007 | Heinl et al. | 5/601 |
| 7,275,273 | B2 * | 10/2007 | Lary et al. | 5/634 |
| 7,290,548 | B2 * | 11/2007 | Ungemach et al. | 128/869 |
| 2002/0165438 | A1 * | 11/2002 | Bartels et al. | 600/300 |
| 2003/0031301 | A1 | 2/2003 | Longton et al. | |
| 2003/0155478 | A1 | 8/2003 | Easterling | |
| 2003/0167569 | A1 | 9/2003 | Newkirk et al. | 5/613 |

* cited by examiner

SYSTEMS FOR IMMOBILIZATION OF A PATIENT FOR DIAGNOSIS AND TREATMENT OF BREAST TISSUE

CROSS-REFERENCE TO RELATED APPLICATION

Claim of Priority: Pursuant to the provisions of 35 U.S.C. §119(e), this application claims the benefit of the filing date of Provisional Patent Application Ser. No. 60/512,551, filed Oct. 17, 2003, for "COMPONENTS AND SYSTEM FOR IMMOBILIZATION OF A PATIENT FOR TREATMENT OF BREAST TISSUE," the contents of which are incorporated by reference herein.

TECHNICAL FIELD

The present invention relates generally to a system and apparatus for positioning patients on a couch top in a precise and repeatable manner for improved diagnosis and treatment of the patient. More specifically, the present invention relates to components and apparatus for use in a breast-board system for positioning patients in a precise and repeatable manner for diagnosis and treatment to increase the comfort of the patient during diagnosis and treatment and improve the accuracy of treatment application.

BACKGROUND

Apparatus for positioning patients in a precise and immobilized manner are often used in treating patients using radiation application therapies. In order to control the application of energy to specific localized areas of a patient; it is necessary to precisely position the patient and ensure that patient movement does not occur during the application of the therapy. Examples of patient positioning systems are provided in U.S. Pat. No. 5,806,116, which issued Sep. 15, 1998 to Oliver et al. and in U.S. Pat. No. 6,161,237, which issued Dec. 19, 2000 to Tang et al., the contents of each of which are incorporated herein in their entireties. These systems use a lock bar arrangement to attach an accessory, such as a face-mask to the table surface to position and immobilize the patient. These references do not teach attachments specifically used for immobilizing a patient in a more comfortable position for treatment of the thorax or torso.

Some breast-boards for positioning and immobilizing a patient for treatment of the torso or thorax are currently available. Examples of some currently available breast-boards include Torsoboards available from Bionix. These boards include a post located at the top of the board, which is grasped by the patient. This grasping places the patient's arm out of the way to allow access to the breast area for treatment. Typically, the post is not adjustable and remains in a single position on the breast-board. A separate U-shaped support on a post may be provided for the upper arm of the patient.

Other available models, such as the MED-TEC MT200, MT250 and MT 350 products lack a grasping-post and instead include a second U-shaped support for the forearm or wrist of the patient. In such embodiments, both U-shaped supports are mounted atop poles, which may be inserted into the board. The position of the upper arm support may be selected by the insertion hole selected, or by the rotation of the support in the hole. The support post may include a plate, or base, through which the post protrudes. A peg-like retaining post may be located on the plate and a rotated position may be maintained by insertion of the peg-like retaining post into a selected retaining hole on the breast-board. Using such embodiments, it may be inconvenient to reposition the support with the patient already on the board. In other embodiments, the peg-like post and retaining holes are absent and a screw clamp is used to retain the support in a selected rotated position. By using a screw clamp, the exact position of the rotation may be difficult to duplicate for subsequent treatments, and the post must be manually held in the desired position as the clamp is tightened.

Of these currently available breast-boards, many are standalone units which are placed on top a standard treatment table. The patient is position with the buttocks on the base of the breast-board, while the upper body lines on the elevated portion. An enlarged "butt stop" located on the proximal end of the breast-board base sits behind the buttocks of the patient. The breast-board is held in position by the weight of the patient thereon. Since the weight of the patient is used to retain the breast-board in place, these boards are typically rigid and a compression of the patient's tissues typically occurs with the weight of the patient is placed thereon. As imaging of the treatment area typically occurs on an imaging table, such as a CT or MRI support table, which holds that patient in a different position than the treatment table, application of treatment radiation to the area must be designed to account for any difference in tissue compression and the change of angle caused by use of a standard breast-board. This can result in the application of treatment radiation to a larger area, than treatment of the specific area of concern may require.

Accordingly, it would be an improvement in the art to provide a breast-board that included supports for the patient's arms that may be used as either a post or as a cupping-support. It would be a further improvement to provide reproducible rotatable positioning for a support that did not use a screw clamp or require the removal and insertion of a peg-like post from the board, allowing additional comfort for a patient. An integrated adjustable support for the tilting of the board may constitute another improvement in the art. Such a breast-board system that is adapted for insertion into, or connection to, both a treatment table and a diagnostic imaging table, in order to provide more consistent imaging and treatment of a patient would be a further improvement in the art.

SUMMARY OF THE INVENTION

The present invention is directed to components of a breast-board system and a breast-board system for use in positioning and immobilizing a patient for treatment. A generally U-shaped wrist support having an unique design with a flattened bottom and rounded post-like tops may be used as either a cupping-support or as a grasping-post by a patient is mounted on a post atop a tiltable breast-board. A second support having a generally U-shaped cross section is mounted on a stand having a base and a supporting framework extending from the base to the support. The base may be rotatably mounted to the tiltable breast-board near the edge thereof. A portion of the base extends over the edge of the breast-board and has a slidable locking mechanism on the bottom surface thereof. The slidable locking mechanism may be retracted by operating a handle on the frame work to slide the mechanism out of one of a number of recesses located on the breast-board. The stand may then be rotated and the slidable locking mechanism actuated by releasing the handle to engage with a recess on the surface. The breast-board system may include a system for supporting the breast-board in a tilted position, including a hinged support member that is may be inserted into a number of preselected positions. The breast-board system may be designed for insertion into a treatment table and for insertion into a diagnostic imaging table. Methods of using the breast-board that allow for better imaging and more accurate treatment are also disclosed and included within the scope of the present invention.

BRIEF DESCRIPTION OF THE DRAWINGS

It will be appreciated by those of ordinary skill in the art that the elements depicted in the various drawings are for exemplary purposes only. The nature of the present invention, including the best mode, as well as other embodiments of the present invention, may be more clearly understood by reference to the following detailed description of the invention, to the appended claims and to the several drawings.

DETAILED DESCRIPTION

The present invention provides components for use in a breast-board system, breast-board systems, and methods of treatment using breast-board systems, which have advantages over those currently used. It will be appreciated by those skilled in the art that the embodiments herein described, while illustrating certain specific and exemplary embodiments, are not intended to limit the invention or the scope of the appended claims. Those of ordinary skill in the art will also understand that various combinations or modifications of the disclosed embodiments may be made without departing from the scope of the invention.

Figure 1:
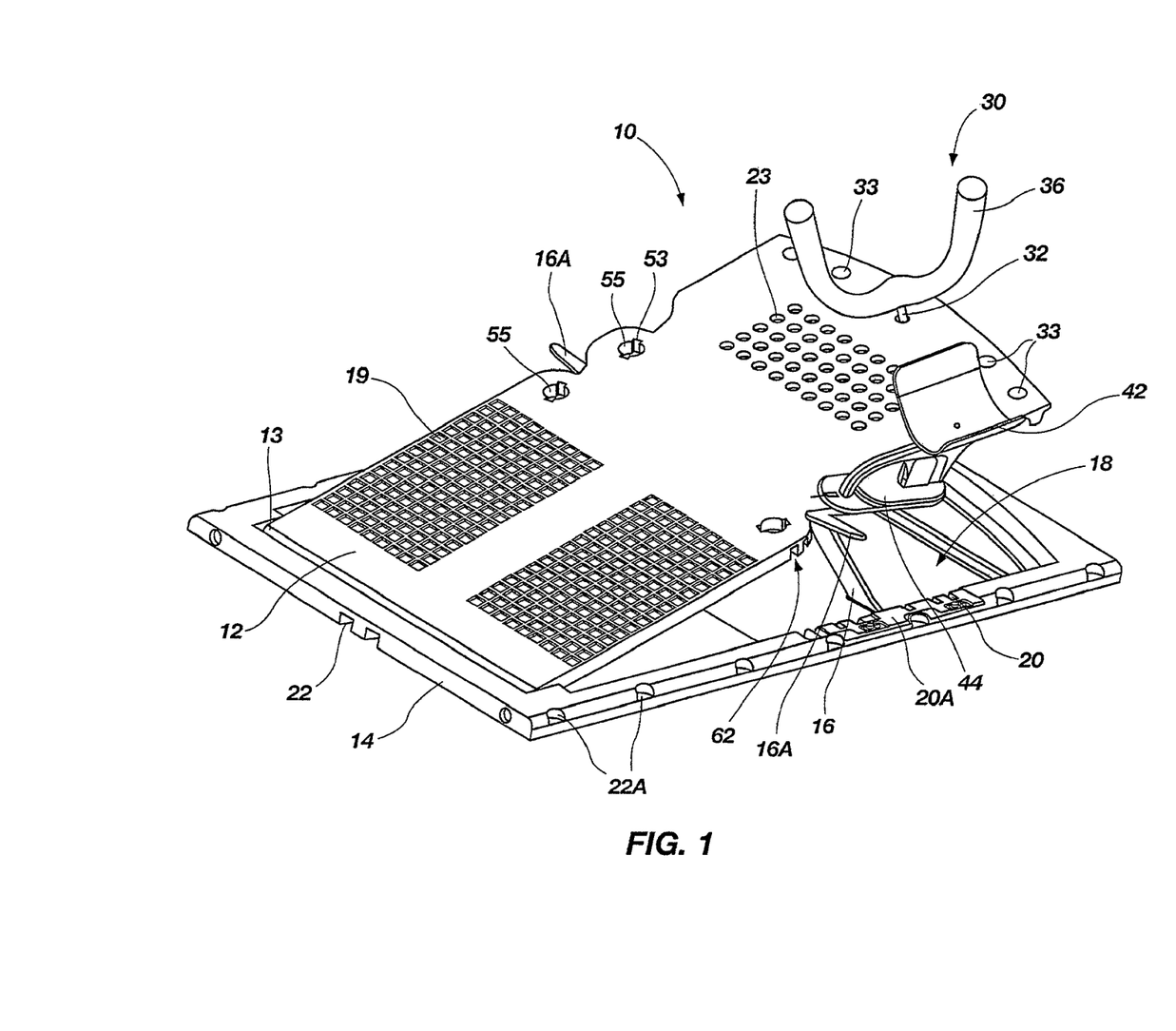
FIG. 1 is a perspective view of an embodiment of a breast-board system in accordance with the principles of the present invention.

FIG. 1 depicts an embodiment of a breast-board system 10 in accordance with the principles of the present invention. The system 10 includes a base board 14, which may be configured for attachment to a patient examining table, or to a patient immobilization system, such as those disclosed in U.S. Pat. Nos. 5,806,116 and 6,161,237, discussed previously herein. Base board 14 may include a recess 18 sized to receive a tilt board 12, when tilt board 12 is in the lowered position.

Connection notches 22 located at the lower end of the base board 14 are one example of a structure that may be used to make a connection to such a system. Any structure required or desirable for making an attachment to a patient examining table or patient immobilization system may be included in a breast-board system 10, in accordance with the present invention. Illustrative examples of such connection structures may include rabbet edges on the base board 14 that correspond to a mating surface around the periphery of a hole in a tabletop, beveled edges on the base board 14, with the wider portion of the bevel at the top surface and a corresponding bevel on the edges of the opening of the tabletop. It will be appreciated that any suitable structure known to those of ordinary skill in the art for attaching an insert may be used.

A second set of notches 22A located along the sides of base board 14 may be used to attach additional accessories to the board in a reproducible manner.

Tilt board 12 is connected to base board 14 by hinges 13 located at the lower end of the tilt board 12 on either long side. The tilt board 12 may be tilted to any desired angle by raising or lowering the upper end, with respect to base board 14. When in the lowered position, the tilt board 12 may lie within recess 18 to form a flat surface, continuous with base board 14. The angle of a desired tilt may be maintained by placing support member 16, which may be attached to the lower surface of tilt board 12 by a hinge, in a support recess 20 selected from a number of similar support recesses 20 on the base board 14. Support recesses 20 and support member 16 may be configured to reside in recess 18, when the tilt board 12 is in the lowered position. It will be appreciated that in some embodiments, support member 16 may be rotatably attached to the base board 14 and the support recesses 20 may be disposed on the lower surface of the tilt board 12. A support member 16 and the corresponding support recesses 20 may be placed on each side of the breast-board system 10. As depicted, two support members 16 and 16A of different lengths are disposed on each side of the tilt board 12, each adjustable for maintaining the tilt board 12 at different heights.

Located on the base board 14 adjacent to the support recesses 20 is a sliding support locking member 20A, which is slidably movable in a direction parallel to the long axis of the side of the base board 14. Once the tip of the support member 16 is inserted in the desired support recess 20, the support locking member 20A may be slid to cover the upper surface of the recess, blockably preventing the removal of the support member 14 tip therefrom. This prevents patient movement from releasing the support member 16. It will be appreciated that a second support member 16, support recesses 20 and support locking member 20A may be disposed on the opposite second edge of the breast-board 10. It will further be appreciated that other mechanisms for retaining the support member 16 tip in the support recess 20 may be used, such as rotatable or removable locking members.

Tilt board 12 may include a flexible support component 19, which is tensioned to provide a predetermined vertical deflection when the weight of a patient is placed thereon. Flexible support component 19 may be a flexible component that can be adjustably tensioned on a frame to adjust the amount of deflection upon load bearing. For example, a suitable filament, e.g., string or yarn may be strung through holes in a frame, similar to the stringing of a tennis racket, or a fabric may be held in place on a frame with a groove and spline, similar to the way a screen window is fixed to a frame. Alternatively, flexible support component 19 may be a grid of a material with a known deflection, such as a carbon fiber grid. Other methods for affixing a flexible support component 19 as part of tilt board 12 will be apparent to those skilled in the art. A pillow or head support may be affixed to the tilt board 12 for the comfort of a patient reclining thereon. The pillow may be affixed to the tilt board 12 by index holes 23, allowing for repeatable precise positioning of the patient.

Figure 2A:
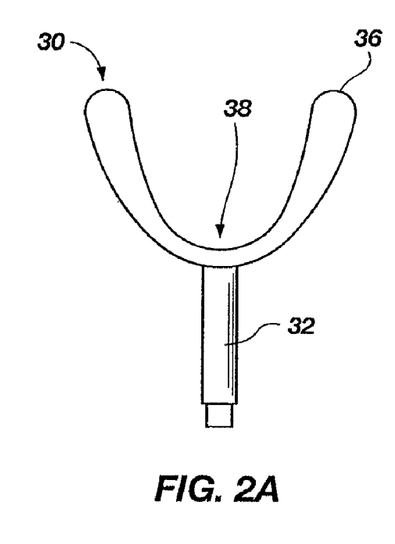
FIGS. 2A, 2B and 2C are front, side and top views, respectively, of embodiments of a wrist support/grasping handle apparatus for use in a breast-board system in accordance with the principles of the present invention.
Figure 2B:
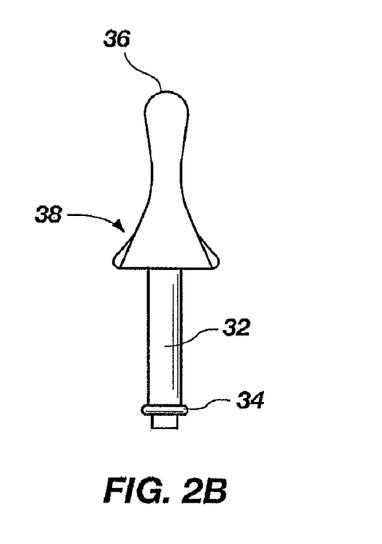
Figure 2C:
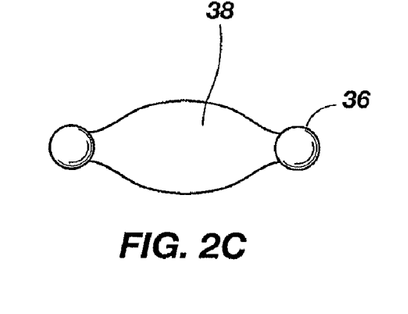

A wrist support/grasping handle 30 may be disposed on the upper surface of the tilt board 12, near the top or distal edge thereof. As best shown in FIGS. 2A, 2B and 2C, the wrist support/grasping handle 30 may be a generally U-shaped support having a central saddle section 38, with a flattened or contoured surface for supporting the wrist of a patient inserted therein. Arising from either end of the central saddle section 38 is a side post 36, which is formed as an extension of a flattened side piece for supporting the wrist of a patient flowing into a post-like upper section having a rounded top. The post-like section may be used by the patient for grasping as a handle. An insertion post 32 may protrude from the bottom of the wrist support/grasping handle 30 and provide for connection to the tilt board 12 through insertion into a selected opening 33 therein. A retaining structure, such as retaining ring 34 (FIG. 2B) may be disposed on the insertion post 32 for retaining the wrist support/grasping handle 30 in the tilt board 12. In some embodiments, the wrist support/grasping handle 30 may be rotatable when inserted. In others; it may retain the relative rotational position of insertion. Instead of a retaining structure, such as retaining ring 34, the insertion post 32 may be retained in a selected opening 33 by a friction fit with the sides thereof. By use of a flexible support component or other "grid" in the tilt board 12, attenuation of a radiation therapy treatment beam may be minimized, where the beam must pass through the tilt board 12.

Figure 3:
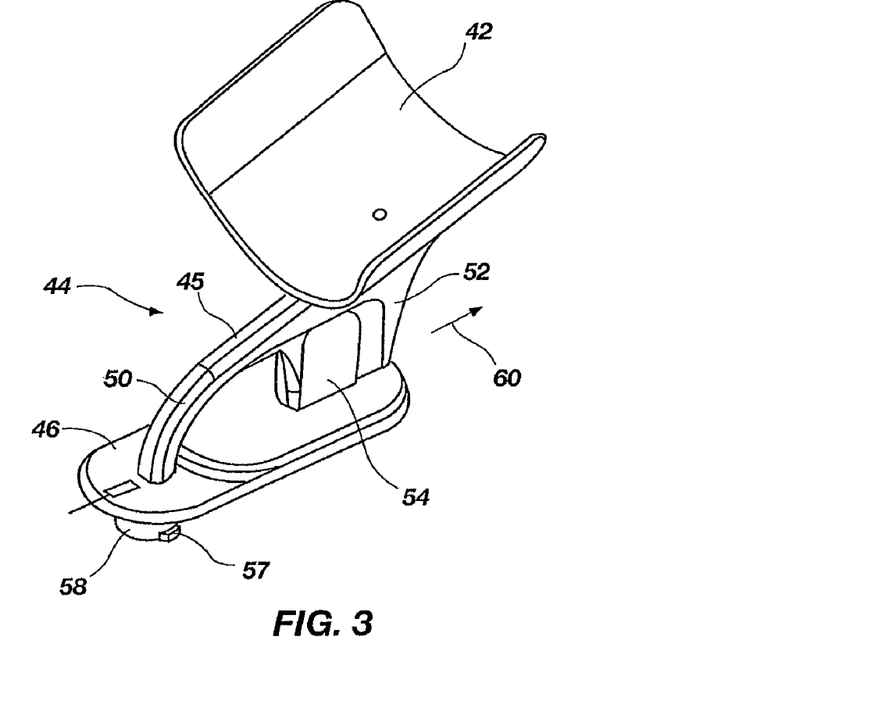
FIG. 3 is a perspective view of an embodiment of an arm support apparatus for use in a breast-board system in accordance with the principles of the present invention.
Figure 4:
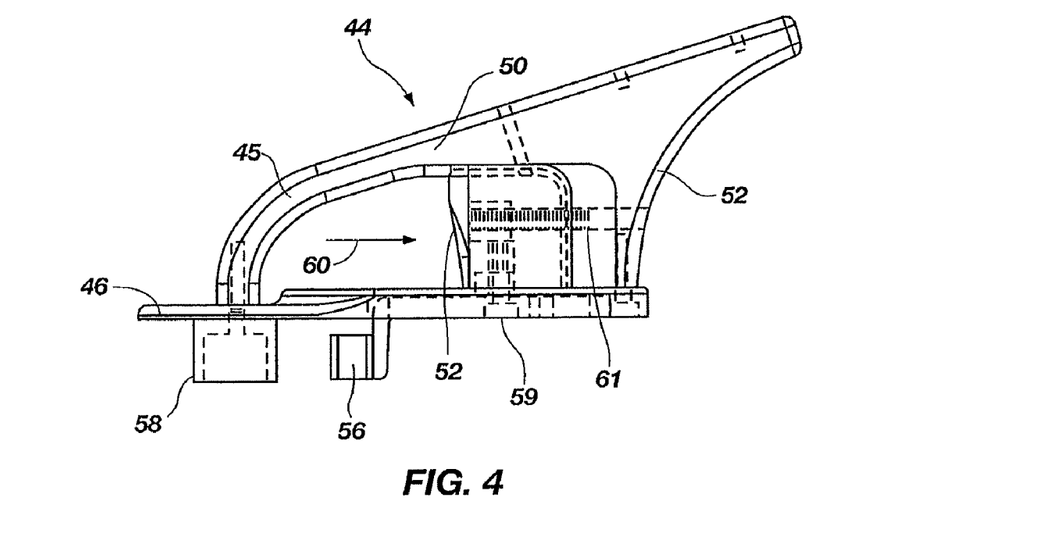
FIG. 4 is a side, cut-a-way view of an embodiment of the framework and base of the arm support apparatus of FIG. 3.
Figure 5:
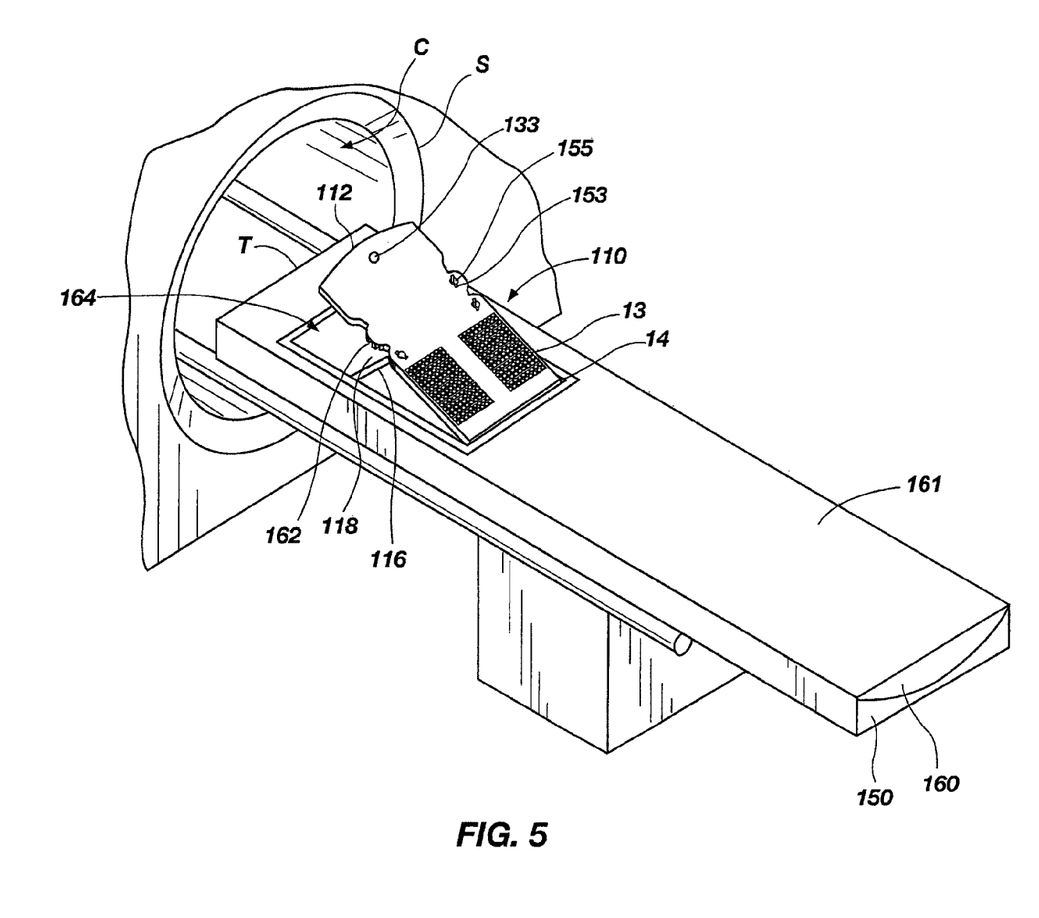
FIG. 5 is a perspective view of an embodiment of a breast-board system in accordance with the principles of the present invention, shown inserted into a diagnostic imaging table top and being readied for diagnostic imaging.
Figure 6:
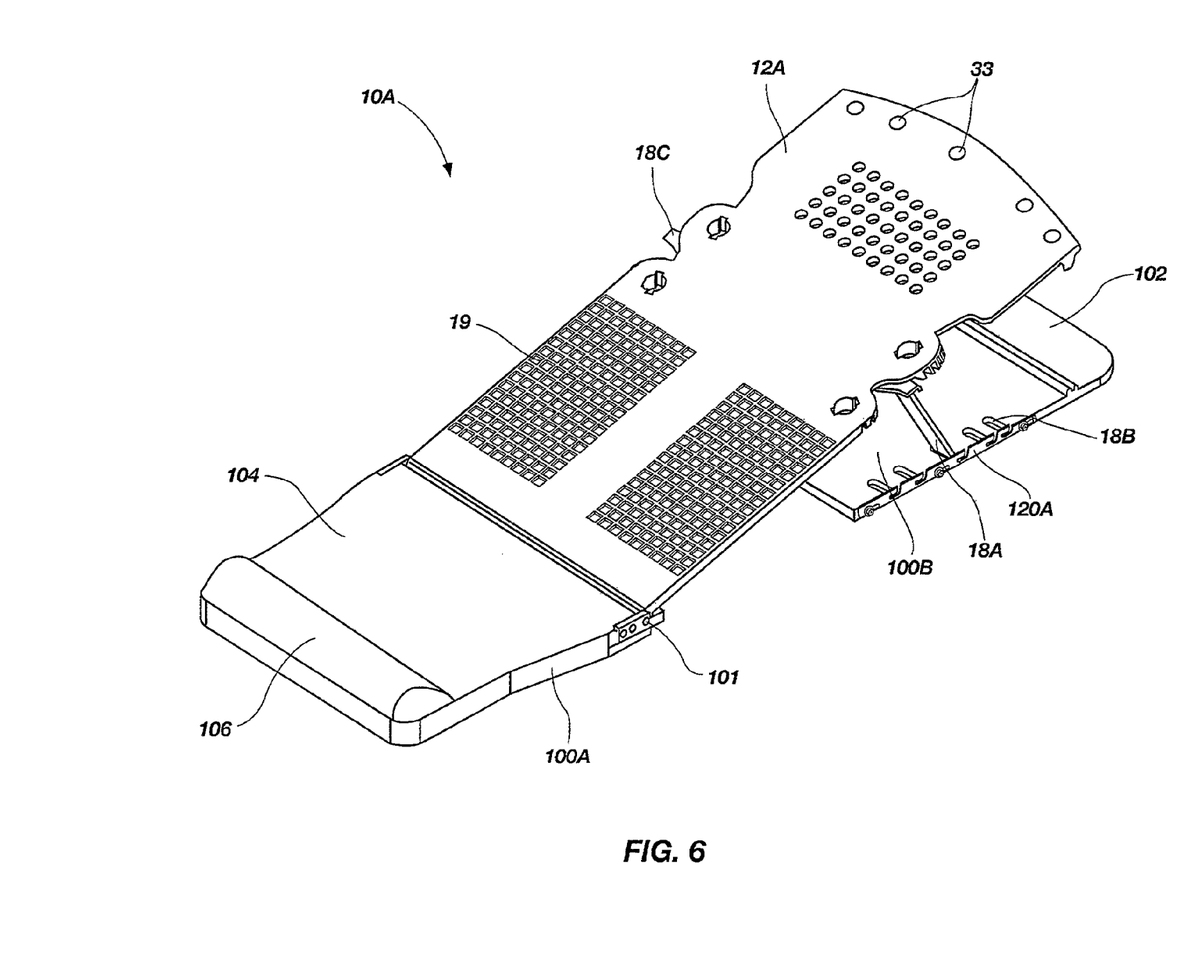
FIG. 6 is a perspective view of another embodiment of a breast-board system in accordance with the principles of the present invention.

Also disposed in on the tilt board 12 in FIG. 1 is an upper arm support 42 mounted on a rotatable stand 44. Additional details of the upper arm support and rotatable stand 44 are depicted in FIGS. 3 and 4. This description of these structures makes reference to FIGS. 1, 3, and 4. Rotatable stand 44 includes a generally flat base 46 and a framework 45. A generally circular insertion member 58 protrudes from the lower surface of the base 46, near the axial end thereof. One or more retention tabs 57 may be disposed on the insertion member 58 to retain the rotatable stand 44 in the tilt board 12. The insertion member 58 may be inserted into a framework insertion hole 55, located near a side edge of the tilt board 12 in a rotatable retaining relationship. Framework insertion hole 55 is best depicted in FIGS. 1, 5 and 6. Framework insertion holes 55 may be placed on opposite side edges of the tilt board 12 to allow use with either arm. In some embodiments, two or more framework insertion holes, with the associated structures may be disposed on each side edge of the tilt board, for added flexibility in usage (FIGS. 1 and 6). In others, only a single framework insertion hole 55 may be present (FIG. 5).

A central section of framework insertion hole 55 allows the insertion member 58 body to pass therethrough, yet is too small to allow the tabs 57 to similarly pass. Framework insertion hole 55 includes bays 53 extending from the central section of the hole 55. Each bay 53 corresponds to a tab 57 and allows passage therethrough, whereupon the stand 44 may be rotated, with the tabs 57 blockably preventing removal of the stand 44, unless aligned with bays 53.

Disposed on the upper side of the base 46 is a framework 45 for supporting an upper arm support 42. Framework 45 as depicted, may include an angled support member 50, which starts near the axial end of the base, and may directly rise from the insertion member 58, passing upwards and angled towards the distal end of the base 46. Near the upper distal end of the angled support member 50, an upper arm support 42 having a generally U-shaped cross section may be mounted, as depicted in FIGS. 1, and 3. It will be appreciated that although the arm support 42 and angled support member 50 are depicted as a member having a round cross-section and rising straight from the base 46, before angling back, with the angle of the arm support 42 determined by the angle of member 50, the depicted framework 45 is exemplary only and any suitable framework to support arm support 42 may be used. Embodiments where the angle of arm support 42 may be adjusted are contemplated as within the scope of the present invention. A second support member 52 including an upright portion and a lateral portion to support the angled support member 50 is depicted in FIGS. 3 and 4, although it will be appreciated that any desired framework 45 may be used.

When rotatable stand 44 is inserted into the tilt board 12, a portion of the base 46 resides away from the tilt board 12. The edge of tilt board 12 in this area may have a rounded edge and include a number of engagement recesses 62 formed therein. A slidable engaging member 56 may be disposed on the lower surface of base 46 to interact with these engagement recesses 62 and retain the framework 44 in a desired position. Slidable engaging member 56 is slidably attached to the lower surface of the base 46, able to move in an axial and distal direction, as by attachment in a channel. A handle 54 may be disposed on the upper surface of the base or on the framework, in order to cause the slidable engaging member 56 to extend or retract. Handle 54 may be formed as a single piece with engagement member 56, or be connected thereto by a suitable linkage, such as that depicted at 59. Additional structures, such as spring 61 for returning the handle 54 and sliding engagement member 56 to the extended position may be included.

In order to rotate the inserted rotatable framework, the slidable engaging member 56 is drawn in the distal direction, ensuring it is free of an engagement recess 62. This may be accomplished by actuating a handle 54 on the upper surface of base 46. In the depicted embodiment, the handle 54 may be squeezed to move in the direction of arrow 60, drawing the engagement member 56 in a distal direction through a linkage therebetween (not depicted). The framework 45 may then be rotated to a desired position and the handle 54 released, sliding the slidable engagement member 56 in the axial position and into an engagement recess 62. The engagement of the slidable engagement member 56 in recess 62 maintains the selected rotational position of the framework 45 and upper arm support 42. A number of engagement recesses 62 are disposed in the edge of tilt board 12, near the insertion hole 55, such that different rotational positions may be selected.

FIG. 5 depicts a diagnostic imaging table T, which may be part of a diagnostic imaging system S, such as a CT imaging system, which includes an imaging chamber C, into which the table is placed for diagnostic imaging of a patient. Often, such diagnostic imaging tables consist of cradles, in which a patient is directed to lay down. As depicted in FIG. 5, a cradle-like table top 150 may have a removable tabletop 160 placed therein to form a flat upper surface 161. It will be appreciated that while reference is made to the removable tabletop 160, a diagnostic imaging system including a table that has a flat top may be utilized in some embodiments of the present invention.

An insertion opening 164 is contained in the tabletop 160, into which a breast-board system 110 may be inserted. When not in use as a breast-board, tilt board 112, may be laid into recess 118 to provide an even table top surface for diagnostic imaging. When in use, the breast-board 112 may be tilted to a desired position and support member 116 actuated to retain it therein. Such an actuation would then appear as depicted in FIG. 5. At that point, a wrist support/grasping handle 30 may be inserted into insertion hole 133, and upper arm support 42, with stand 44 may be inserted into framework insertion hole 155, with tabs 57 passing through bays 153. Slidable engagement member 56 may be inserted into the desired recess 162. The breast-board 110 is appropriately sized to pass into chamber C and allow imaging of a patient disposed thereon.

Imaging of the patient may then take place, allowing a treatment protocol to be designed. A corresponding breast-board system, having the same attributes of that installed in the diagnostic imaging table T, or even the same breast-board 110 that is installed in the diagnostic imaging table T during patient imaging, may then used during the application of treatment radiation. In this manner, diagnostic imaging of the patient's tissue may a produce a detailed image for patient treatment that has tissue compression and patient angling and immobilization that more exactly correspond to the patient's condition in actual treatment.

In use, a patient is typically placed face-up on the elevated tilt board 12 or 112, with at least one arm extended upwards using an upper arm support 42 and wrist support/grasping handle 30. This maintains the patient in a selected position for imaging or for application of treatment radiation to the thoracic region. For example, radiation treatment for breast cancer or other cancer on the torso may be provided. The breast-board system 10, in conjunction with upper and lower arm supports, discussed further herein, can maintain the patient in the same position for imaging and multiple treatments, easing design of treatment plans. As discussed in connection with the embodiment of FIG. 5, the use of a breast-board system 10 in accordance with the principals of the present invention in imaging as well as treatment allows for more accurate treatment planning.

Depicted in FIG. 6 is another embodiment of a breast-board system 10A in accordance with the teachings of the present invention. Components of the system that are the same as that depicted in FIG. 1 are labeled with the identical reference numerals. Where the embodiment of FIG. 1 is intended for use as a component inserted into a patient examination table or a diagnostic imaging table, breast-board system 10A is a freestanding system that may be used in connection with any preexisting patient examination table or couch. Tilt board 12A is rotatably attached to a base board 100A through a pivot joint or hinge 101. Base board 100A includes an extended hip board 104 portion underlies the hips of a patient using the breast-board system 10A, which may be formed separate from an upper base board 100B. Alternatively, the upper and lower base boards 100B and 100A may be formed as a single piece with an associated recess. A padded roll 106 may be located on the hip board 104 for the comfort of the patient. A support portion 102 of the base board (depicted as upper base board 100B) underlies the top end of tilt board 12A. Support member 18A or 18C may extend from tilt board 12A, from the lower surface thereof to support portion 102 to interact as previously described herein with support recesses 18B to maintain the desired angle for treatment.

It is noted that the sliding support locking member 120A is located on the side of upper base board 100B adjacent to the support recesses 18B and is slidably movable in a direction parallel the long axis of the side of the upper base board 100B. Once the tip of the support member 18A is inserted in the desired support recess 18B, the support locking member 120A may be slid to cover the side surface of the recess, blockably preventing the removal of the support member 18A tip therefrom. This prevents patient movement from releasing the support member 18A. It will be appreciated that a second support member 18A, support recesses 18B and support locking member 120A may be disposed on the opposite second edge of the breast-board system 10.

Breast-board systems in accordance with the present invention may be offered as sets, including all necessary breast-board components, such as the base and tilt board as a construct, along with one or more wrist support/grasping handles 30 and one or more upper arm supports 42. Such a set may even include a removable tabletop 160. Alternatively, all components may be offered separately for use with other systems or as replacement parts.

It will be apparent that details of the apparatus, processes, and methods herein described can be varied considerably without departing from the concept and scope of the invention. The claims alone define the scope of the invention as conceived and as described herein.

What is claimed is:

1. A breast-board system sized and adapted to attach to a radiation therapy table comprising:
   a unitary base board;
   a planar tilt board having an upper end and a lower end, the lower end being attached to the unitary base board, the planar tilt board being configured to fully support a thoracic portion of a body of a patient, the planar tilt board being rotatable relative to the unitary base board between a first position in which the planar tilt board is oriented generally parallel to the unitary base board and at least one additional position in which the planar tilt board is oriented at an angle to the unitary base board;
   at least one movable support member extending between the unitary base board and the planar tilt board, the at least one movable support member supporting the planar tilt board relative to the unitary base board when the planar tilt board is in the at least one additional position, and the at least one movable support member having a portion movable in a longitudinal direction relative to the unitary base board;
   at least one support recess in the unitary base board for receiving the portion of the at least one movable support member therein when the planar tilt board is in the at least one additional position, the portion of the at least one movable support member at least partially in contact with the unitary base board; and
   at least a first support locking member located on the unitary base board adjacent to the at least one support recess and movable between a first position and a second position, the at least a first support locking member at least partially covering the at least one support recess and preventing removal of the portion of the at least one movable support member from the at least one support recess when the at least a first support locking member is in the first position, the portion of the at least one movable support member being removable from the at least one support recess when the at least a first support locking member is in the second position.

2. The breast-board system of claim 1, further comprising an arm support comprising:
   an insertion member configured for insertion into an insertion opening in the planar tilt board, the insertion member being rotatable between two or more rotational positions relative to the planar tilt board when the insertion member is inserted into the insertion opening in the planar tilt board; and
   a locking device configured to selectively lock the arm support in the two or more rotational positions.

3. The breast-board system of claim 2, wherein the arm support further comprises a handle disposed on a top surface of a base and in communication with the locking device, such that actuation of the handle will cause the locking device to withdraw from a retaining recess located in an edge of the planar tilt board, when the base is mounted thereon.

4. The breast-board system of claim 3, wherein the arm support further comprises a supporting framework extending from the base to the handle disposed on a top surface of the base, the handle disposed on a top surface of the base and in communication with the locking device disposed on the supporting framework.

5. The breast-board system of claim 4, further comprising a wrist support component that may be releasably attached thereto, the wrist support component comprising a central saddle section including a curved area, a first side post attached to a first side of the central saddle section and extending as a continuation of the curved area thereof, and a second side post attached to a second side of the central saddle section opposite the first side, the second side post extending as a continuation of the curved area of the central saddle section.

6. The breast-board system of claim 5, wherein the wrist support component further comprises an insertion post extending from a lower surface thereof, opposite the central saddle section, and configured for insertion into a wrist support attachment opening in the breast-board to releasably attach thereto.

7. The breast-board system of claim 6, wherein the planar tilt board being rotatable relative to the unitary base board comprises two or more wrist support attachment openings for receiving a wrist support component.

8. The breast-board system of claim 6, wherein the wrist support is configured to rotate about a vertical axis defined by the insertion member and perpendicular to the planar tilt board.

9. The breast-board system of claim 1, wherein the at least a first support locking member is slidably movable in a direction parallel to the longitudinal axis of the base board.

10. The breast-board system of claim 1, further comprising at least one structure for attachment to a radiation therapy treatment tabletop comprising one or more connection notches corresponding to one or more structures on the radiation therapy treatment tabletop.

11. The breast-board system of claim 1, wherein the unitary base board includes a recess where the planar tilt board can reside in a lowered position.

12. The breast-board system of claim 1, wherein the unitary base board comprises a lower hip board portion with a support member separate from an upper portion of the unitary base board.

13. The breast-board system of claim 2, wherein the insertion member comprises a locking tab, and the insertion opening includes a central portion configured to allow only the insertion member to pass therethrough and a bay through which the locking tab may pass when aligned therewith to reside on an opposite surface of the planar tilt board.

14. The breast-board system of claim 2, wherein the planar tilt board being rotatable relative to the unitary base board comprises one or more insertion openings for receiving an insertion member.

15. The breast-board system of claim 2, wherein the arm support is configured to rotate about a vertical axis defined by the insertion member and perpendicular to the planar tilt board.

* * * * *

UNITED STATES PATENT AND TRADEMARK OFFICE
CERTIFICATE OF CORRECTION

| | | |
|---|---|---|
| PATENT NO. | : 7,836,890 B2 | |
| APPLICATION NO. | : 10/968368 | |
| DATED | : November 23, 2010 | |
| INVENTOR(S) | : Glenn N. Waterman | |

It is certified that error appears in the above-identified patent and that said Letters Patent is hereby corrected as shown below:

On the title page:
Item (*Primary Examiner—*)　　　change "Michael A. Brown" to --Patricia Bianco--

Signed and Sealed this
Twelfth Day of March, 2013

Teresa Stanek Rea
*Acting Director of the United States Patent and Trademark Office*